United States Patent
Neas et al.

(10) Patent No.: US 11,246,807 B2
(45) Date of Patent: Feb. 15, 2022

(54) OXIDATIVE COMPOSITIONS AND METHODS FOR STIMULATING THE GROWTH OF OSTEOBLASTS AND USE IN DENTAL COATINGS AND JAW BONE AUGMENTATION

(71) Applicant: Armis Biopharma, Inc., Fort Collins, CO (US)

(72) Inventors: Edwin Neas, Nunn, CO (US); Scott Noblitt, Fort Collins, CO (US)

(73) Assignee: ARMIS BIOPHARMA, INC., Fort Collins, CO (US)

( * ) Notice: Subject to any disclaimer, the term of this patent is extended or adjusted under 35 U.S.C. 154(b) by 126 days.

(21) Appl. No.: 16/629,232

(22) PCT Filed: Jul. 7, 2018

(86) PCT No.: PCT/US2018/041165
§ 371 (c)(1),
(2) Date: Jan. 8, 2020

(87) PCT Pub. No.: WO2019/010467
PCT Pub. Date: Jan. 10, 2019

(65) Prior Publication Data
US 2020/0129383 A1    Apr. 30, 2020

Related U.S. Application Data

(60) Provisional application No. 62/529,854, filed on Jul. 7, 2017, provisional application No. 62/529,838, filed on Jul. 7, 2017.

(51) Int. Cl.
| | | |
|---|---|---|
| *A61K 6/69* | (2020.01) | |
| *A61C 8/02* | (2006.01) | |
| *A61K 31/19* | (2006.01) | |
| *A61K 33/06* | (2006.01) | |
| *A61K 33/40* | (2006.01) | |

(52) U.S. Cl.
CPC .............. *A61K 6/69* (2020.01); *A61C 8/0006* (2013.01); *A61K 31/19* (2013.01); *A61K 33/06* (2013.01); *A61K 33/40* (2013.01)

(58) Field of Classification Search
CPC ...... A01N 37/42; A01N 59/00; C07C 407/00; A61K 45/06; A61K 31/327; A61K 33/44; A61K 31/13
See application file for complete search history.

(56) References Cited

U.S. PATENT DOCUMENTS

| | | |
|---|---|---|
| 6,355,663 B1 | 3/2002 | Harada et al. |
| 7,708,558 B1 | 5/2010 | Hall et al. |
| 2009/0257914 A1 | 10/2009 | Christopher et al. |
| 2010/0082072 A1 | 4/2010 | Sybert et al. |
| 2013/0330397 A1 | 12/2013 | Neas et al. |
| 2015/0306064 A1 | 10/2015 | Neas et al. |
| 2017/0303538 A1* | 10/2017 | Neas ..................... A61K 31/365 |

FOREIGN PATENT DOCUMENTS

WO   2009120969   10/2009

OTHER PUBLICATIONS

Extended European Search Report dated Mar. 11, 2021, issued in European Application No. 18827567.1 (6 pages).
International Search Report and Written Opinion dated May 17, 2019, issued in Application No. PCT/US2018/041165 (15 pages).

* cited by examiner

*Primary Examiner* — Walter E Webb
(74) *Attorney, Agent, or Firm* — Fox Rothschild LLP

(57) ABSTRACT

Clinical application of oxidative compositions, alone or in combination with polymer or salt stabilizers, for use in bone proliferation applications, such as spinal surgery, arthroplasty, or osteosarcoma. Additional applications include use in dental artificial tooth implants, orthopedic implantable prostheses for small and large bones, implantation into other surgical sites (e.g., dental implants, bone graft additive, face reconstruction, etc.) where bone growth is desired.

19 Claims, No Drawings

OXIDATIVE COMPOSITIONS AND METHODS FOR STIMULATING THE GROWTH OF OSTEOBLASTS AND USE IN DENTAL COATINGS AND JAW BONE AUGMENTATION

CROSS-REFERENCE TO RELATED APPLICATIONS

The present application claims priority under 35 U.S.C. § 119(e) to U.S. Provisional Patent Application Ser. Nos. 62/528,854 and 62/529,838, both of which were filed on Jul. 7, 2017. The disclosures of both applications are incorporated by reference herein in their entirety.

BACKGROUND

Bone is a dynamic tissue that is constantly being reshaped by osteoblasts, which produce and secrete matrix proteins and transport minerals into the matrix, and osteoclasts, which break down the tissue. The osteoclasts are the only cell type other than osteoblasts and osteocytes that are structural components of bone, although within the hollow inside of bones are many other cell types of the bone marrow. Components of the bone marrow that are essential for osteoblast bone formation include mesenchymal stem cells, the precursors of osteoblasts, and blood vessels which supply oxygen and nutrients for bone formation. Bone is a highly vascular tissue, and active formation of blood vessel cells, also from mesenchymal stem cells, is essential to support the metabolic activity of bone.

There are more than 30,000 orthopedic implant revision surgeries necessary each year in part due to poor implant fixation with juxtaposed bone. A further emphasis on the current problems associated with insufficient bone implant performance is the fact that many patients are receiving hip implants earlier in life, remaining active older, and that the human lifespan is continuously increasing. Collectively, it is clear that there is a strong clinical need to improve implant performance through proper, prolonged fixation. Because of the important role of osteoblasts in the healing and regeneration processes of bone, an ability to enhance the proliferation of these cells and improve the bone implant fixation remains a desirable objective. Natural bone insufficiency can be caused by: gum disease, tooth development defects, wearing dentures long term, an injury to the face or trauma, spaces left empty in the mouth after teeth are removed, and dental procedures where efforts were not made to restore natural bone.

Dental implants are artificial tooth roots inserted into the jaw to replace missing teeth. Today, implants with attached crowns are the preferred method for treating tooth loss because they function the same as natural teeth and help preserve the jaw structure by preventing atrophy from bone loss. Permanent implants maintain proper chewing function and exert appropriate, natural forces on the jawbone to keep it functional and healthy.

Implants are generally titanium screws a dentist inserts into the jawbone and affixes a prosthetic tooth or crown. Titanium implants over time fuse naturally with bone, a process known as osseointegration. Implant surgery can replace one or more teeth provided there is sufficient bone to support the implants. Would-be implant patients should have the procedure done as soon as possible after losing a tooth to prevent bone loss at the site. However, often, titanium implants fail to fuse with the bone or the patient does not have the ability to efficiently grow the jawbone (i.e. elderly patients).

Several techniques are used to rebuild bone. Bone grafting is a safe and highly successful procedure that involves the "building up" or adding bone. Bone is built up in the jaw by using the patient's own natural bone from another location and/or by using a donor, processed or synthetic bone materials. Often the new bone can be obtained from inside the mouth. Implants will be placed after the grafted bone has fused or become a strong, integrated part of the existing bone. The amount of time the integration takes varies depending on the location of the graft and the density of the bone. It may take three or more months.

Sinus Lift (Sinus Augmentation or Sinus Elevation) is a procedure used when the back teeth in the upper jaw are missing the sinus cavity becomes larger as the natural bone deteriorates over time. A sinus lift, also called sinus augmentation or sinus elevation, is a bone-augmentation procedure for patients who have insufficient natural bone in this area for dental implant placement. The procedure involves adding bone below the sinus so that one or more implants can be placed. After the bone has been given time to develop, usually for approximately four to 12 months, dental implants can be placed. Ridge Expansion (Ridge Modification) is a procedure where bone graft material can be added to a small ridge, or space, that is created along the top of the jaw. In some situations implants can be placed right after a ridge expansion. Other situations require approximately four to 12 months to ensure that the ridge has fully healed first.

Because the time to grow new jaw bone is rather long, patients have to wait up to 12 months to have tooth implants. It is therefore desirable to speed up the "building-up" of the jaw bone and to reduce the amount of time for bone graft integration. Likewise, it is also desirable to add a coating to the titanium implants that may generate new bone growth and bone calcification.

SUMMARY OF THE INVENTION

Compositions and methods that play an important role in osteoblasts healing and regeneration of bone cells are disclosed. The present embodiments are directed to methods of stimulating the growth of osteoblast cells by application of a composition that comprises one or more of a peroxyacid, a bis(hydroperoxide), a hydroperoxide, or an epoxide.

In one aspect of the present invention, a method for stimulating the growth of osteoblast cells is provided, in which a composition containing a mixture of a peracid and a bis(hydroperoxide), in an amount sufficient to stimulate osteoblast growth, is applied to the osteoblast cells.

According to another aspect of the present invention, a method for stimulating bone growth in a patient in need thereof is provided, in which the patient is administered an amount of a composition containing a mixture of a peracid and a bis(hydroperoxide), in an amount effective to initiate a significant increase in bone mass. According to one embodiment, the composition is delivered locally to a bone wound or defect.

According to another aspect of the present invention, a method for stimulating the growth of osteoblast cells is provided, in which osteoblast cells are cultured in the presence of a composition containing a peracid and a bis(hydroperoxide) in an amount sufficient to stimulate osteoblast growth.

According to another aspect of the present invention, a method of inducing membranous bone formation is provided, in which a composition containing a mixture of a peracid and a bis(hydroperoxide) is applied to a tissue proximate to membranous bone in an amount effective to induces membranous bone formation.

According to another aspect of the present invention, a method of increasing the rate of bone formation in vertebrate tissue is provided, in which a composition containing a mixture of a peracid and a bis(hydro-peroxide) is applied to the tissue in an amount sufficient to increase the rate of bone growth at a rate faster than treatment without the mixture.

According to another aspect of the present invention, a method for increasing bone calcification in a patient in need thereof is provided, in which a composition containing a mixture of a peracid and a bis(hydroperoxide) is administered to the patient in an amount effective to provide an increase in bone mass calcification.

According to another aspect of the present invention, a method for restoring and regenerating jaw bone is provided, in which a composition containing a mixture of a peracid and a bis(hydroperoxide) in applied directly to a bone socket missing a tooth in an amount sufficient to stimulate osteoblast growth in the socket. According to one embodiment, the mixture is applied to the bone socket in a liquid form. According to another embodiment, the mixture is applied to the bone socket in a powder form.

According to yet another aspect of the present invention, a method for replacing a missing tooth is provided, in which an artificial dental implant in combination with a composition containing a mixture of a peracid and a bis(hydroperoxide) is inserted directly into the jaw to replace missing tooth. According to one embodiment, the mixture is coated on the implant. According to another embodiment, the quantity of the mixture is sufficient to promote an increased rate of fixation by inducing the overall osteogenic activity of bone growth substances.

According to another aspect of the present invention, a method for repairing trauma to the jaw bone or face is provided, in which an artificial dental implant in combination with a composition containing a mixture of a peracid and a bis(hydroperoxide) is inserted directly into the face bone. According to one embodiment, the composition is coated on the dental implant. According to another embodiment, the quantity of said composition is effective to promote an increased rate of fixation by inducing the overall osteogenic activity of bone growth substances.

According to another aspect of the present invention, a method for treating a dental trauma is provided, in which the trauma includes an empty bone socket where a tooth used to be and a resorbable or non-resorbable membrane is inserted inside the bone socket, wherein the membrane is combined with a composition containing a mixture of a peracid and a bis(hydroperoxide). According to one embodiment, the composition is coated on the membrane. According to another embodiment, the quantity of the composition is effective to promote an increased rate of fixation by inducing the overall osteogenic activity of bone growth substances.

In each of the foregoing aspects of the invention, the composition may further contains a hydro-peroxide, an epoxide, or both. In one embodiment, the composition contains an oxidizing agent. In another embodiment the peracid and bis(hydroperoxide) are used in synergistic quantities to stimulate bone growth. In yet another embodiment the composition is formulated as a gel, liquid, beads, film, coating, or a combination thereof.

The foregoing features and other advantages will be apparent from the following detailed description.

DETAILED DESCRIPTION OF THE PREFERRED EMBODIMENT

The compositions of the invention, and their method of preparation, are disclosed in commonly owned International Application No. PCT/US18/41163, filed on the same date as the present application. The disclosure of PCT/US18/41163 is incorporated by reference herein in its entirety.

In some embodiments, the composition may comprise a peroxyacid and a bis(hydroperoxide). In some embodiments, the composition further comprises a hydroperoxide. In other embodiments, the composition further comprises an epoxide. In some embodiments, the composition comprises peracetic acid and 3,3-bis(hydroperoxy)butanoic acid. In other embodiments, the composition comprises peracetic acid and 3,3-bis(hydroperoxy)butaneperoxoic acid. In other embodiments, the composition further comprises at least one of methyl hydroperoxide and hydroxymethyl hydroperoxide. In some embodiments, the composition further comprises 5-hydroperoxy-5-methyl-1,2-dioxolan-3-one. In some embodiments, the composition further comprises hydrogen peroxide.

In some embodiments, composition further comprises peroxycitraconic acid. The peroxycitraconic acid may be either (2Z)-4-hydroperoxy-3-methyl-4-oxobut-2-enoic acid, (2Z)-4-hydroperoxy-2-methyl-4-oxobut-2-enoic acid, or a mixture thereof. In other embodiments, the compositions may comprise diperoxycitraconic acid, i.e., (2Z)-2-methylbut-2-enediperoxoic acid. In other embodiments, the antimicrobial composition further comprises peroxycitramalic acid. The peroxycitramalic acid may be either 4-hydroperoxy-2-hydroxy-2-methyl-4-oxobutanoic acid, 4-hydroperoxy-3-hydroxy-3-methyl-4-oxobutanoic acid, or a mixture thereof.

In some embodiments, the composition may comprise 3,3-bis(hydroperoxy)butanoic acid, 3,3-bis(hydroperoxy) butaneperoxoic acid, or 3-oxobutaneperoxoic acid, or a mixture thereof. In other embodiments, the compositions further comprise 5-hydroperoxy-5-methyl-1,2-dioxolan-3-one. In some embodiments, the composition further comprises one or more of hydrogen peroxide, an organic hydroperoxide, an organic peroxide, an organic peracid, an inorganic peracid, an organic acid, or an inorganic acid. In some embodiments, the composition further comprises hydrogen peroxide.

In some embodiments, the composition may comprise acetoacetic acid, or a salt of acetoacetic acid. The salt of acetoacetic acid may be a lithium, sodium, potassium, rubidium, cesium, zinc, magnesium, or calcium salt. The composition may further comprise a hydroperoxide, including hydrogen peroxide and/or an organic hydroperoxide. In other embodiments, the composition may further comprise a keto acid. The keto acid may be an alpha-, beta-, or gammaketo acid. In some embodiments, the composition may further comprise pyruvic acid, parapyruvic acid, or citramalic acid, any of their salts, or mixtures thereof. In other embodiments, the composition may further comprise an acetoacetate ester such as methyl acetoacetate, ethyl acetoacetate, or acetoacetic anhydride. In some embodiments, the composition further comprises hydrogen peroxide.

In some embodiments, the composition may comprise hydroperoxyacetic acid. In other embodiments, the composition further comprises hydrogen peroxide.

In other embodiments, the composition is made by a method comprising contacting a keto acid or a salt or anhydride thereof with an oxidizing agent while stirring and under conditions sufficient to produce one or more of a peroxyacid, a hydroperoxide, a bis(hydroperoxide), or an epoxide. In some embodiments, the conditions are sufficient to produce a peroxyacid and a bis(hydroperoxide). In some embodiments, the conditions are sufficient to produce a peroxyacid, a hydroperoxide, a bis(hydroperoxide), and an epoxide.

In some embodiments, the keto acid may be an alpha-, beta-, or gamma-keto acid. In other embodiments, the keto acid is an alpha-keto acid. In some embodiments, the keto acid is pyruvic acid or a salt, ester, or anhydride thereof. In other embodiments, the keto acid is parapyruvic acid or a salt, ester, or anhydride thereof. In other embodiments, the keto acid is acetoacetic acid or a salt or anhydride thereof. In some embodiments, the keto acid salt may be a lithium, sodium, potassium, rubidium, cesium, zinc, magnesium, or calcium salt, or a mixture thereof. In other embodiments, the process further comprises contacting the keto acid or salt thereof and the oxidizing agent with maleic acid or anhydride, citraconic acid or anhydride, or a mixture thereof.

In some embodiments, the reaction temperature is about 10° C. or less. In other embodiments, the reaction temperature ranges from about −40° C. to 10° C. In some embodiments, the molar ratio of oxidizing agent to keto acid typically ranges from 1:1 to about 1000:1.

In one embodiment, the method comprises adding a keto acid or salt or anhydride thereof to an oxidizing agent with stirring at a shear rate between about 150 and about 850 $sec^{-1}$ to form a reaction solution. In another embodiment, prior to adding the keto acid or salt or anhydride thereof, the oxidizing agent is cooled to between −40° C. to 0° C., and the keto acid or salt or anhydride thereof is added at a rate sufficient to maintain the temperature of the resulting mixture between −40° C. to 0° C. during addition of the keto acid or salt or anhydride thereof. A shear rate between about 150 and about 850 $sec^{-1}$ equates to stirring at a rate between about 90 and about 500 RPM. In some embodiments, the method further comprises continually stirring the reaction solution for 10 to 12 hours at a temperature between −40° C. to 0° C. In other embodiments, the method further comprises warming the reaction solution to between 14° C. and 27° C. In some embodiments, the method further comprises maintaining this temperature for 30 days. In some embodiments, the oxidizing agent is hydrogen peroxide and the keto acid is pyruvic acid.

In some embodiments, the composition may be made by a method comprising contacting citramalic acid or a salt, ester, on anhydride thereof with an oxidizing agent while stirring under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide. In some embodiments, the citramalic acid salt may be a lithium, sodium, potassium, rubidium, cesium, zinc, magnesium, or calcium salt, or a mixture thereof. In other embodiments, the process further comprises contacting citramalic acid or salt, ester, or anhydride thereof and the oxidizing agent with acetic acid or anhydride thereof, maleic acid or anhydride thereof, citraconic acid or anhydride thereof, or a mixture thereof.

In another embodiment, the composition may be made by a method comprising contacting an acetoacetate ester or a salt thereof with an oxidizing agent while stirring under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide. In some embodiments, the acetoacetate ester may be methyl acetoacetate or ethyl acetoacetate, or a mixture thereof. In other embodiments, the acetoacetate ester salt may be a lithium, sodium, potassium, rubidium, cesium, zinc, magnesium, or calcium salt, or a mixture thereof. In some embodiments, the process further comprises adding citramalic acid.

In another embodiment, instead of reacting a keto acid or a salt or anhydride thereof with an oxidizing agent under the conditions described herein to produce the disclosed mixture of compounds, the present invention also provides compositions that are admixtures of the key composition components, Compositions according to this embodiment contain hydrogen peroxide, a peracid, such as peracetic acid, and one or more optional compounds selected from tartaric acid, formic acid, cis-epoxysuccinic acid, methyltartaric acid, acetic acid, cis-epoxymethylsuccinic acid, maleic acid, citramalic acid and citraconic acid. Compositions according to this embodiment of the present invention may also optionally include oxidized acetoacetate compounds.

While a variety of oxidizing agents may be used in such methods, typical oxidizing agents may comprise hydrogen peroxide, sodium peroxide, barium peroxide, sodium carbonate peroxide, potassium superoxide, a peracid, or a mixture thereof. In some embodiments, the oxidizing agent is hydrogen peroxide.

In general, peracids are compounds of oxidized form of a base organic acid (generally a carboxylic acid) that exist in equilibrium with an oxidizer (generally hydrogen peroxide) and water. Peracids may be oxidized from other carboxylic acids, e.g. citric acid, succinic acid, short chain fatty acids, etc.

The amount of peracid and bis(hydroperoxide) in the composition may vary depending on a variety of factors including the type of bone fracture to be treated, type of implant, the coating of the implant material etc.

Peracids (peroxycarboxylic or percarboxylic) acids generally have the formula $R(CO_3H)n$, where, for example, R is an alkyl, aryl, arylalkyl, cycloalkyl, aromatic, or heterocyclic group, and n is one, two, or three, and named by prefixing the parent acid with peroxy. The R group can be saturated or unsaturated as well as substituted or unsubstituted. Peroxycarboxylic acids can be made by the direct action of an oxidizing agent on a carboxylic acid, oxidation of an ester, by autoxidation of aldehydes, or from acid chlorides, and hydrides, or carboxylic anhydrides with hydrogen or sodium peroxide.

The combination of a peracid and a bis(hydroperoxide) is believed to produce a synergistic effect, providing a strong cellular response in healthy osteoblasts and therefore promoting healthy jaw bone growth. The presence of acetoacetic acid, or other keto acids, and/or titanium compounds such as titanium salts, organotitanium compounds and titanium metal implants, including titanium dental implants may contribute to the synergistic effect. In addition, the combination of a peracid and a bis(hydroperoxide) or any of the compositions described above can kill high levels of bacteria and spores in biofilms and in high-protein environments. Furthermore, the combination has low corrosivity and presents lower cellular toxicity issues. The said mixture of a peracid and a bis(hydroperoxide) avidly binds growth factors, and increases the rate and degree to which bone formation is induced. The mixture of peracids may accomplish this by increasing the residency rates of bone growth factors and by inducing calcification of chondrogenic, osteogenic and osteoblastic cells.

Accordingly, in one embodiment, the invention may include a method of treatment with oxidative agents for maintaining bone homeostasis, enhancing bone formation and/or enhancing bone repair.

In one embodiment, the invention includes methods and devices for increasing the residency times of bone inducing substances. In one embodiment, the invention includes methods and devices for increasing the rate and overall osteogenic activity of bone inducing substances. Further, in one embodiment, the invention includes methods and devices for reducing time required for the effect of osteogenesis and calcification of bone-inducing substances.

Some aspects of the invention provide methods for treating a bone fracture comprising contacting the bone fracture with a therapeutically effective amount of a composition comprising a peracid and a bis(hydroperoxide), or any of the compositions described above. In some aspects, the present invention also relates to oxidative compositions and mixtures thereof, as well as methods for making and using any of the compositions described above. In one embodiment, the composition is applied directly to the bone in a liquid form. In one embodiment, the composition is admixed with a bone putty or cement containing autologous bone tissue, xenograft bone tissue, cadaver bone tissue or a synthetic bone material containing hydroxyapatite or a like ceramic material. The putty or cement may contain other substances effective to promote osteogenesis such as bone morphogenic proteins.

Within another embodiment, the cells are grown in vitro in an oxidative composition mixture. Within one embodiment, the composition may be stabilized and coated on various type of bone implants, including dental implants by adding various organic co-polymers such as poly(lactic-co-glycolic acid) PLGA, polycaprolactone (PCL), polyethylene glycol (PEG), polyarylether ketones; and other generic copolymers.

Some aspects of the invention provide treatment methods in which the disclosed compositions are used in combination with titanium compounds. Suitable titanium compounds include titanium salts, organotitanium compounds and titanium metal implants, including orthopedic titanium implants.

In one embodiment, coatings are applied directly to implants with polymer or metal surfaces in a liquid solution or suspension. Within another embodiment, the composition is combined with a polymer by solvent or melt processing or in situ polymerization and coated on the polymer or metal surface.

Coatings according to the present invention have a tendency to lose their antimicrobial activity over time, which is believed to be the result of evaporation of the neat peracid. One aspect of the present invention adds a magnesium salt to the composition to form a salt of the peracid, which testing has shown to retain antimicrobial activity over a lengthy accelerated aging test. Accordingly, compositions according to the present invention further include a magnesium salt. The magnesium salt can be a salt of the keto acid, or a magnesium salt such as magnesium, hydroxide, magnesium carbonate, magnesium acetate tetrahydrate, and the like.

Some aspects of the invention provide methods for treating a jaw bone comprising contacting the bone jaw with a therapeutically effective amount of a composition comprising a peracid and a bis(hydroperoxide), or any of the compositions described above. In some aspects, the present invention also relates to oxidative compositions and mixtures thereof, as well as methods for making and using compositions comprising mixtures of a peracid and a bis (hydroperoxide), or any of the compositions described above. In one embodiment, the composition is applied directly to the bone in a liquid form. Within another embodiment, the cells are grown in vitro in an oxidative composition mixture.

Bone Augmentation

Bone augmentation is a procedure for restoring or regenerating bone in tooth sockets that would not be able to support implant placements without augmentation. Sufficient bone mass is critical for implant surgery success. In one embodiment, the invention discloses a method for jaw bone augmentation, using an oxidative mixture of a peracid and a bis(hydroperoxide), and epoxide, or any of the compositions described above, for maintaining bone homeostasis, enhancing bone formation and/or enhancing bone repair.

In one embodiment, the invention includes methods and devices for increasing the residency times of bone-inducing substances. In one embodiment, the invention includes methods and devices for increasing the rate and overall osteogenic activity of bone inducing substances. Further, in one embodiment, the invention includes methods and devices for reducing time required for the effect of osteogenesis and calcification of bone-inducing substances.

Some aspects of the invention provide methods for treating jaw bone loss comprising contacting the bone socket with a therapeutically effective amount of a composition comprising an oxidative mixture comprising a peracid and a bis(hydroperoxide), or any of the compositions described above. In some aspects, the present invention also relates to oxidative compositions and mixtures thereof, as well as methods for making and using compositions comprising a peracid and a bis(hydroperoxide), or any of the compositions described above. In one embodiment, the composition is applied directly to the bone in a liquid form directly to the bone socket. Within another embodiment, the oxidative composition is powdered and mixed with the bone additive. In another embodiment, the disclosed compositions are used in combination with titanium compounds. Suitable titanium compounds include titanium salts, organotitanium compounds and titanium metal implants, including orthopedic titanium implants.

Coated Dental Implants

Implants are generally titanium screws a dentist inserts into the jawbone and affixes a prosthetic tooth or crown. Titanium implants over time fuse naturally with bone, a process known as osseointegration. In one embodiment, the invention discloses a method for dental implant fixation, using an oxidative mixture of a peracid and a bis(hydroperoxide), or any of the compositions described above for maintaining bone homeostasis, enhancing bone formation and/or enhancing bone repair. In one embodiment, the invention includes methods for coating a dental bone implant with a polymeric coating comprising an oxidative mixture of a peracid and a bis(hydroperoxide), or any of the compositions described above, in order to achieve an increased rate of implant fixation by inducing the overall osteogenic activity of bone growth substances.

Some aspects of the invention provide methods for treating jaw bone loss comprising contacting a jaw bone implant with a therapeutically effective amount of a composition comprising an oxidative mixture of a peracid and a bis (hydroperoxide), or any of the compositions described above. In one embodiment, the composition is applied directly to the implant in a liquid. In another embodiment, the oxidative composition is polymerized and coated on the dental bone implant.

Coatings for Dental Plates and Screws

Dental plates and screws are generally titanium screws and plates a dentist inserts into the jawbone and face to repair certain trauma that occurs in the jaw bone or face. The plates and screws fuse naturally with bone, during a process known as osseointegration. In one embodiment, the invention discloses a method for dental screws and plates fixation, using an oxidative mixture of a peracid and bis(hydroperoxide), or any of the compositions described above, for maintaining bone homeostasis, enhancing bone formation and/or enhancing bone repair. In one embodiment, the invention includes methods for coating a dental screws and plates with a polymeric coating comprising an oxidative mixture of a peracid and bis(hydroperoxide), or any of the compositions described above, in order to achieve an increased rate of fixation by inducing the overall osteogenic activity of bone growth substances.

In one embodiment, the composition is applied directly to the dental screw or plate in a liquid form. Within another embodiment, the oxidative composition is polymerized and coated on the dental plate and the dental screws.

Coatings for Resorbable and Non-Resorbable Membranes.

A membrane is a barrier used to prevent gum from growing into the bone cavity. On many bone grafts for dental implants, a membrane is placed over the bone but under the gum. In one embodiment the invention includes methods for coating resorbable and non-resorbable membranes with a polymeric coating comprising an oxidative mixture of a peracid and a bis(hydroperoxide), or any of the compositions described above, in order to achieve an increased rate of fixation by inducing the overall osteogenic activity of bone growth substances.

In one embodiment, the composition is applied directly to the membrane in a liquid form. Within another embodiment, the oxidative composition is polymerized and coated on the resorbable or non-resorbable membrane.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

Example

The present invention is described more fully by way of the following non-limiting examples. Modifications of the examples will be apparent to those skilled in the art.

Shelf-stable coatings containing the magnesium salt of peroxyacetic acid were prepared by drying solutions containing a magnesium salt, acetic acid, hydrogen peroxide, peracetic acid, and poly(ethylene glycol) (PEG). The starting magnesium salt was magnesium hydroxide, magnesium carbonate, or magnesium acetate tetrahydrate (an anhydrous magnesium acetate salt would also be effective since it is being dissolved in a water-containing mixture). The acetic acid/hydrogen peroxide/peracid source was an aqueous solution (called "PAA Source" in this document) usually containing 8-12 wt % peracid (peracetic acid), 15-22 wt % hydrogen peroxide, and 14-20 wt % acetic acid. Coatings were also be made in the presence of silica particles (up to 2.8%). Finally, the remainder of the solution typically consisted of water, but the short-chain alcohols methanol, ethanol, and isopropanol were also successfully used, with the shortest chains being the most successful.

A typical coating-solution mixture consisted of the following, which was used immediately after mixing:

4.1 wt % magnesium acetate tetrahydrate
20 wt % PAA Source
20 wt % PEG 3350
55.9 wt % water Magnesium acetate tetrahydrate concentrations in the 1.8-6.5 wt % range were used successfully, with the best peracid recoveries occurring at higher concentrations. PAA Source concentrations of 8-72 wt % were found to yield stable peracid salts. PEG concentrations of 0-30 wt % were tested successfully. PEG 3350 and PEG 8000 both yielded coatings containing stable peracid salts.

Coatings were made in two distinct ways. In the first, a small aliquot of coating solution (typically 20 µL) was placed onto a flat substrate and allowed to dry at room temperature (~20° C.), 40° C., 55° C., or 60° C. In the second method, the solution was pumped through a nozzle and sprayed onto a tumbling set of substrates. The spray-based instrument is termed a pan coater, and here was a Thomas Engineering Compu-Lab with a 1×¼" JAU gun and 40100 AB spray nozzle with a 15" coating pan. Drying air was 30-55° C. at 240-300 ft$^3$/min. Solution spraying accomplished with atomization air at 10-16 psi with a fluid-spray rate of 1.5-3.5 mL/min. Pan rotation speed was 16-24 rpm. Note that in both preparation methods the relative humidity must be below the deliquescence point of the coating (approximately 35% relative humidity for the PEG 3350-based coatings) in order to completely dry and for proper storage. High temperatures are not problematic as long as the temperature is maintained below the melting point of the coating (~56° C. for coatings comprised of PEG 3350).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights that include alternative embodiments to the extent permitted, including alternate, interchange-able and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for stimulating the growth of osteoblast cells comprising:
   applying to the cells a composition comprising a mixture of a peracid and a bis(hydro-peroxide), in an amount sufficient to stimulate osteoblast growth.

2. A method according to claim 1, wherein the composition further comprises a hydro-peroxide, an epoxide, or both.

3. A method according to claim 1, wherein the composition further comprises an oxidizing agent.

4. A method according to claim 1, wherein the peracid and bis(hydroperoxide) are used in synergistic quantities to stimulate bone growth.

5. A method according to claim 1, wherein said composition is formulated as a gel, liquid, beads, film, coating, or a combination thereof.

6. A method for stimulating bone growth in a patient in need thereof, comprising administering to said patient a composition comprising a mixture of a peracid and a bis(hydro-peroxide), in an amount effective to initiate a significant increase in bone mass, wherein the composition is administered by local delivery to a bone wound or defect.

7. The method of claim 1, wherein the mixture further comprises a magnesium salt.

8. The method of claim 7, wherein the magnesium salt is magnesium acetate tetrahydrate.

9. The method of claim 1, wherein the cells are cultured in the presence of the composition.

10. The method according to claim 6, wherein the composition is delivered to the bone wound or defect by applying the composition to a tissue proximate the bone wound or defect.

11. The method according to claim 6, wherein the bone wound or defect is on or in a bone socket missing a tooth.

12. A method according to claim 11, wherein the mixture is administered in at least one of a liquid form, or a powder form.

13. A method for replacing a missing tooth comprising inserting an artificial dental implant in combination with a mixture of a peracid and a bis(hydroperoxide) directly into the jaw at the site of a bone trauma or in a bone socket missing a tooth.

14. The method of claim 13, wherein the mixture is coated on the implant.

15. The method of claim 13, wherein the quantity of said mixture is sufficient to promote an increased rate of fixation by inducing the overall osteogenic activity of bone growth substances.

16. A method for repairing trauma to a jaw bone or face bone, the method comprising inserting an artificial dental implant comprising a mixture of a peracid and a bis(hydroperoxide) directly into the jaw bone or face bone at the site of a bone trauma or in a bone socket missing a tooth.

17. The method of claim 16, wherein the mixture is coated on the dental implant.

18. The method of claim 16, wherein the dental implant comprises the mixture on or in a resorbable or non-resorbable membrane.

19. A bone implant characterized by a polymer or metal surface coated with a composition comprising a mixture of a peracid and a bis(hydro-peroxide) and a magnesium salt, in an amount sufficient to stimulate osteoblast growth.

* * * * *